(12) United States Patent
Somasundaram

(10) Patent No.: US 7,028,356 B2
(45) Date of Patent: *Apr. 18, 2006

(54) MULTICONFIGURATION BRAKING SYSTEM

(75) Inventor: Baskar Somasundaram, Bangalore (IN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 45 days.

This patent is subject to a terminal disclaimer.

(21) Appl. No.: 10/379,122

(22) Filed: Mar. 4, 2003

(65) Prior Publication Data

US 2004/0172757 A1    Sep. 9, 2004

Related U.S. Application Data

(63) Continuation-in-part of application No. 10/065,866, filed on Nov. 26, 2002.

(51) Int. Cl.
*A61G 13/00*    (2006.01)

(52) U.S. Cl. .................................. 5/607; 5/610; 5/600
(58) Field of Classification Search .................... 5/600, 5/607, 610, 611
See application file for complete search history.

(56) References Cited

U.S. PATENT DOCUMENTS

| | | | |
|---|---|---|---|
| 1,118,851 A * | 11/1914 | Turner | 108/142 |
| 1,444,042 A * | 2/1923 | Schwalbach | 108/20 |
| 3,588,500 A | 6/1971 | Koerner | |
| 3,944,204 A | 3/1976 | Cesar | |
| 4,013,019 A | 3/1977 | Horsey | |
| 4,071,222 A | 1/1978 | Wright | |
| 4,435,862 A | 3/1984 | King et al. | |
| 4,452,439 A | 6/1984 | Hogan | |
| 4,475,072 A | 10/1984 | Schwehr et al. | |
| 4,484,571 A | 11/1984 | Velazquez | |
| 4,541,108 A | 9/1985 | Grady et al. | |
| 4,597,119 A * | 7/1986 | Padgett | 5/656 |
| 4,715,591 A | 12/1987 | Dragmen | |
| 4,731,889 A | 3/1988 | Ishikawa | |
| 4,751,754 A | 6/1988 | Bailey et al. | |
| 4,761,000 A | 8/1988 | Fisher et al. | |
| 4,769,584 A | 9/1988 | Irigoyen et al. | |
| 4,771,785 A | 9/1988 | Duer | |
| 4,841,585 A | 6/1989 | Masuzawa | |
| 4,908,844 A | 3/1990 | Hasegawa | |
| 4,912,754 A | 3/1990 | Van Steenburg | |
| 4,944,500 A | 7/1990 | Mueller et al. | |
| 5,013,018 A | 5/1991 | Sicek et al. | |
| 5,014,292 A | 5/1991 | Siczek et al. | |
| 5,048,071 A | 9/1991 | Van Steenburg | |
| 5,131,105 A | 7/1992 | Harrawood et al. | |

(Continued)

FOREIGN PATENT DOCUMENTS

DE    EPO 268 555 B1    10/1986

(Continued)

*Primary Examiner*—Sunil Singh
(74) *Attorney, Agent, or Firm*—McAndrews, Held & Malloy, Ltd.; Peter J. Vogel; Michael A. Dellapenna

(57) ABSTRACT

Certain embodiments include a system and method for braking in a patient positioning system. The system includes a patient positioning surface for supporting a patient, a first brake for affecting motion of the patient positioning surface, and a second brake for affecting motion of the patient positioning surface. In an embodiment, the first brake is a power-off brake that is active when power is removed from the brake. The second brake is a power-on brake that is active when power is applied to the brake. Power may be applied and/or removed from the first and second brakes o affect the motion of the patient positioning surface.

8 Claims, 6 Drawing Sheets

U.S. PATENT DOCUMENTS

| | | |
|---|---|---|
| 5,156,166 A | 10/1992 | Sebring |
| 5,205,004 A | 4/1993 | Hayes et al. |
| 5,210,893 A | 5/1993 | Uosaki et al. |
| 5,237,600 A | 8/1993 | Kamata |
| 5,272,776 A | 12/1993 | Kitamura |
| 5,386,453 A | 1/1995 | Harrawood et al. |
| 5,398,356 A | 3/1995 | Pfleger |
| 5,572,569 A | 11/1996 | Benoit et al. |
| 5,590,429 A | 1/1997 | Boomgaarden et al. |
| 5,596,779 A | 1/1997 | Meek |
| 5,659,909 A | 8/1997 | Pfeuffer et al. |
| 6,038,718 A | 3/2000 | Pennington et al. |
| 6,094,760 A | 8/2000 | Nonaka et al. |
| 6,192,585 B1 | 2/2001 | Buchanan et al. |
| 6,240,582 B1 | 6/2001 | Reinke |
| 6,249,695 B1 | 6/2001 | Damadian |
| 6,269,499 B1 | 8/2001 | Amir |
| 6,334,708 B1 | 1/2002 | Kosugi |
| 6,353,949 B1 | 3/2002 | Falbo |
| 6,470,519 B1 * | 10/2002 | Pattee et al. .................... 5/600 |
| 6,541,973 B1 | 4/2003 | Danby et al. |
| 6,566,833 B1 * | 5/2003 | Bartlett ........................ 318/564 |
| 6,615,428 B1 | 9/2003 | Pattee |
| 6,615,429 B1 | 9/2003 | Weil et al. |
| 6,651,279 B1 * | 11/2003 | Muthuvelan .................... 5/600 |
| 6,769,145 B1 * | 8/2004 | Pfeuffer et al. ................. 5/601 |
| 6,769,806 B1 | 8/2004 | Moyers |
| 6,857,147 B1 | 2/2005 | Somasundaram |
| 2002/0029419 A1 | 3/2002 | Weil et al. |
| 2002/0120986 A1 | 9/2002 | Erbel et al. |
| 2003/0053599 A1 | 3/2003 | Meyer et al. |
| 2003/0145383 A1 | 8/2003 | Schwaegerle |
| 2004/0028188 A1 | 2/2004 | Amann et al. |
| 2004/0098804 A1 * | 5/2004 | Varadharajulu et al. ......... 5/611 |
| 2004/0139545 A1 * | 7/2004 | Reinke et al. ................. 5/86.1 |
| 2004/0172756 A1 | 9/2004 | Somasundaram |
| 2004/0172757 A1 | 9/2004 | Somasundaram |
| 2004/0172758 A1 | 9/2004 | Alakkat |

FOREIGN PATENT DOCUMENTS

| | | |
|---|---|---|
| EP | 119910 | 6/1988 |

* cited by examiner

Up-Down & Rotation (Patient Loading)

Longitudinal Travel (Scanning)

Longitudinal Tilt (Vascular Tilt)

Longitudinal Axis

Head Up tilt (Positive)

Head Down tilt (Negative)

Highest Postion

Lowest Postion

Fwd. Tilt Position

Reverse Tilt Position

HEAD - DOWN TILT

HEAD - UP TILT

ISO-CENTER TRACKING

Cross Section of Power-on Brake

Cross Section of Power-off Brake

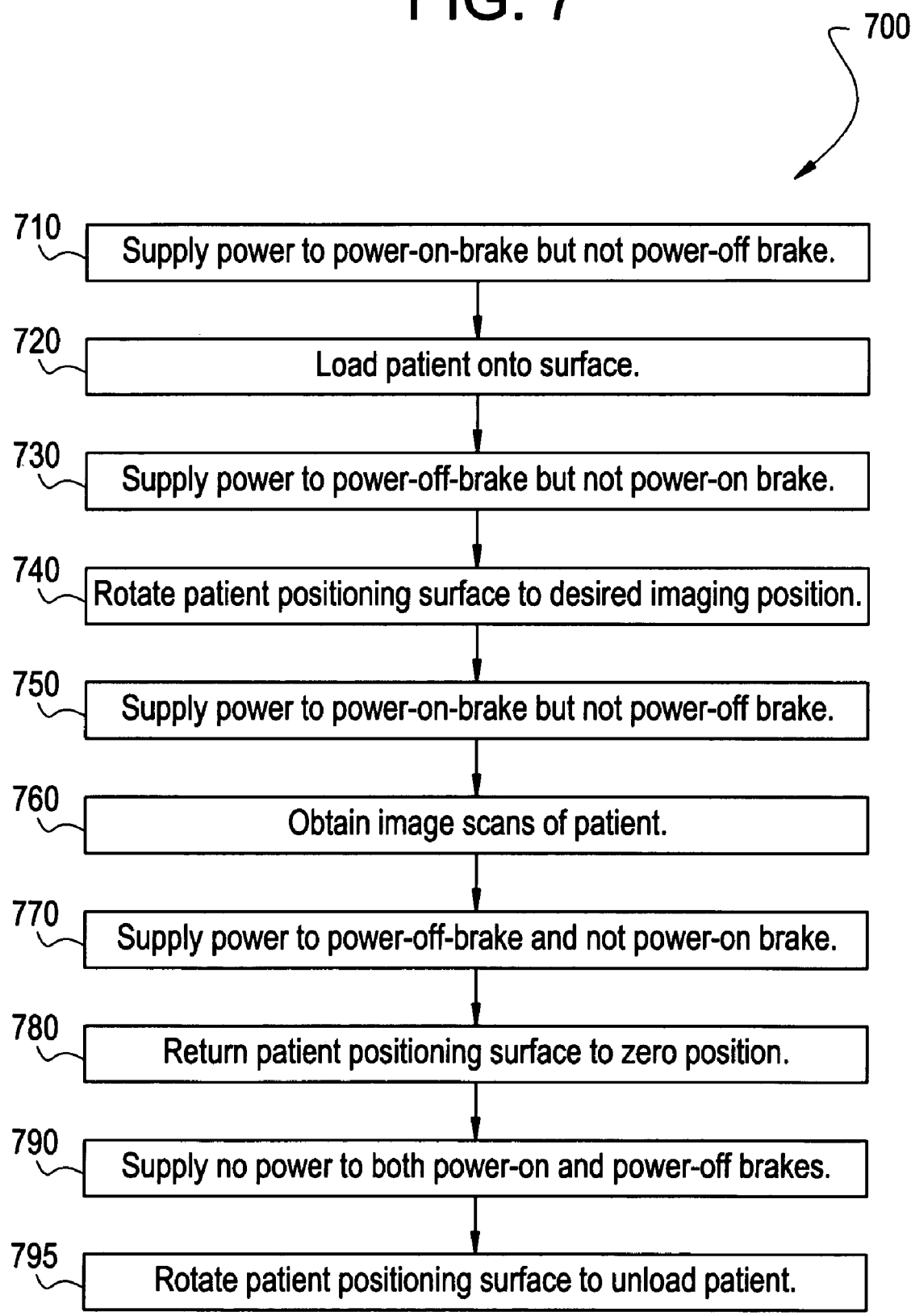

MULTICONFIGURATION BRAKING SYSTEM

RELATED APPLICATIONS

This application is a continuation-in-part of U.S. application Ser. No. 10/065,866, filed Nov. 26, 2002, titled "Grouted Tiltint Patient Positioning Table For Vascular Applications."

RELATED APPLICATIONS

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention generally relates to braking in a patient positioning system. In particular, the present invention relates to safe and effective braking at the rotational axis in a patient positioning system.

Patient positioning platforms allow a medical practitioner, such as a doctor, nurse or technician, to position a patient during a medical procedure, such as XR, CT, EBT, nuclear, and PET procedures. Patient positioning platforms, such as tables or other supports, allow a patient to be elevated, moved in lateral and longitudinal directions, rotated and/or tilted during a procedure. Patient positioning platforms improve a medical practitioner's ability to examine and/or perform a medical procedure on a patient.

There is a need for an improved patient positioning platform that may be used in angiography, neurology, and cardiac procedures. Current patient positioner platforms may introduce limitations in obtaining images of blood flow in arteries, heart, lungs, or brain, for example. Thus, a patient positioning system that improves stability and reliable positioning for blood flow imaging in angiography, neurology, cardiac and other such procedures would be highly desirable. Additionally, a patient positioning system that provides reliable and easy positioning of a patient with flexibility to accommodate a variety of medical procedures and emergencies would be highly desirable.

An improved patient positioning platform is capable of performing complex motions to position a patient. During such complex motions, it may be desirable to stop motion of the patient positioning platform. For example, the patient positioning platform may be stopped for emergency treatment of the patient, repositioning of the patient, or manual movement of the patient positioning platform. Additionally, there is a need for a braking system of minimal size that will hold the patient positioning platform. Furthermore, a braking system that reduces power consumption when stopping or holding the patient positioning platform would be highly desirable.

Thus, a need exists for a method and system for braking in a patient positioning system.

BRIEF SUMMARY OF THE INVENTION

Certain embodiments include a system and method for a multiconfiguration braking and rotation system in a patient positioning system. The braking and rotation system includes a patient positioning surface for supporting a patient, a lift subsystem for adjusting elevation of the patient positioning surface, a longitudinal subsystem for moving the patient positioning surface in a longitudinal direction, a tilt subsystem for tilting the patient positioning surface, and a rotation subsystem for rotating the patient positioning surface. The system also includes a first brake and a second brake for securing the patient positioning surface. The system further includes a position sensor for determining a position of the patient positioning surface and a control subsystem for controlling operation of the patient positioning system. In an embodiment, the first brake is a power-off brake that is active when power is removed from the power-off brake. The second brake is a power-on brake that is active when power is applied to the power-on brake. The system may also include lateral subsystem for moving the patient positioning surface in a lateral direction.

In an embodiment, a bull gear and pinion are used in combination with the first brake and the second brake to secure the patient positioning surface. The first brake and the second brake may secure the patient positioning surface using interlocking teeth. The first brake and the second brake may be used in combination to secure the patient positioning surface. The first brake may be mounted on a first pinion and the second brake may be mounted on a second pinion.

In an embodiment, the first and second brakes may be used in at least three states. In the first state, a 100% capacity state, both first and second brakes are activated. In the second state, a 50% capacity state, the first brake is released, and the second brake is activated. In the third state, a 0% capacity state, both first and second brakes are released.

The method includes applying or removing power at a first brake, applying or removing power at a second brake, and affecting motion of a patient positioning surface with the first and second brakes. In an embodiment, the first brake is a power-off brake, and the second brake is a power-on brake. The method may also include moving the patient positioning surface to a desired position. Additionally, the method may include halting movement of the patient positioning surface if a clearance distance between the patient positioning surface and an object is less than or equal to a minimum safe clearance distance. A gear and pinion system may be used with the first and second brakes to affect rotation motion of the patient positioning surface.

In an embodiment, the first brake and second brake may be used in at least three states to affect motion of the patient positioning system. The three states include a 100% capacity state with the first and second brakes activated, a 50% capacity state with the first brake released and the second brake activated, and a 0% capacity state with the first and second brakes released.

In an embodiment, a rotational axis braking system for a patient positioning surface includes a patient positioning surface for supporting a patient, a first brake for affecting motion of the patient positioning surface, and a second brake for affecting motion of the patient positioning surface. The system may further include a position sensor for determining a position of the patient positioning surface and a control subsystem for controlling operation of the patient positioning surface. In an embodiment, the first brake is a power-off brake that is active when power is removed from the brake. The second brake is a power-on brake that is active when power is applied to the brake.

BRIEF DESCRIPTION OF SEVERAL VIEWS OF THE DRAWINGS

FIG. 7 illustrates a flow diagram for braking in a patient positioning system in accordance with an embodiment of the present invention.

Figure 1A:
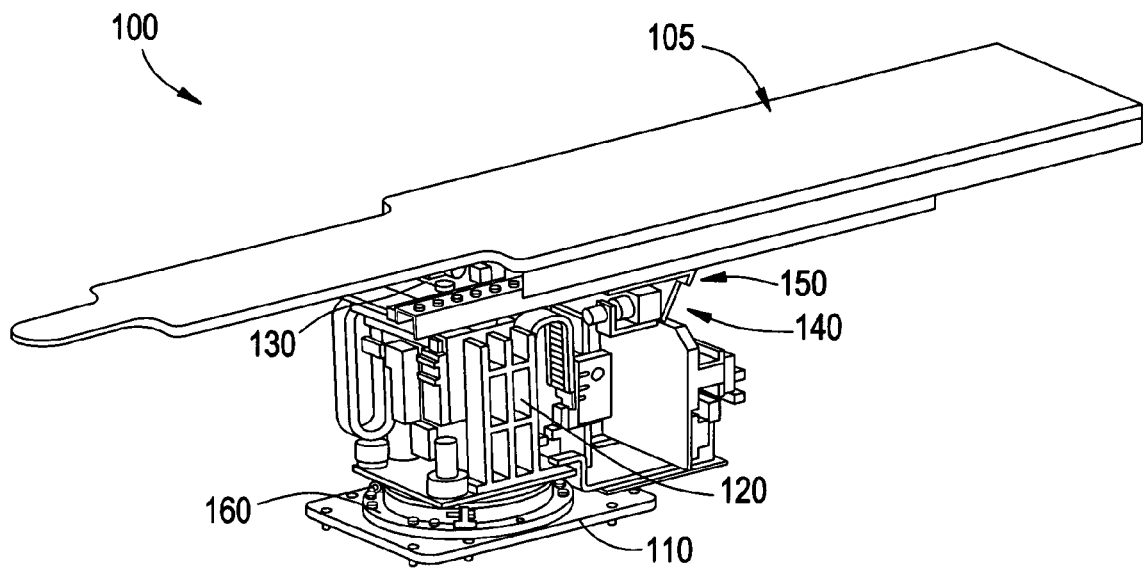
FIGS. 1A and 1B illustrate a patient positioning system that is used in accordance with an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Figure 1B:
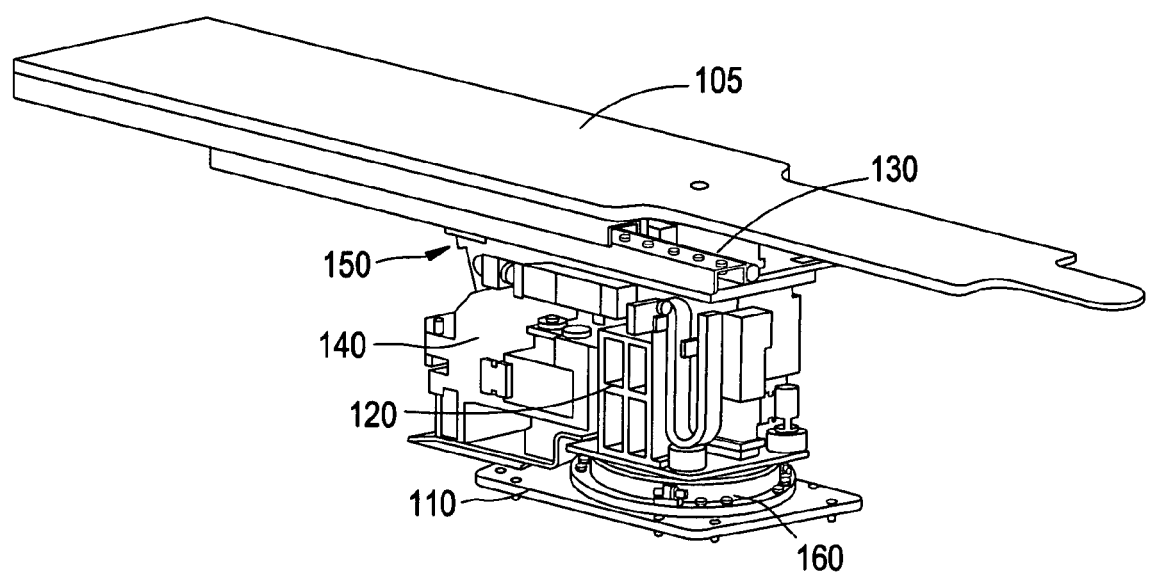
Figure 2A:
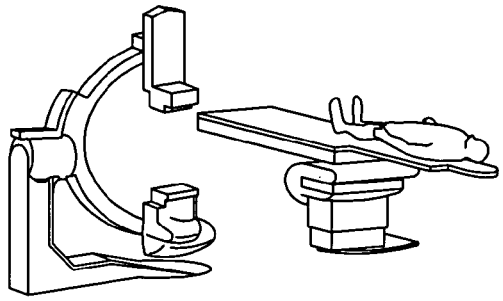
FIGS. 2A. 2K 2C and 2D illustrate positions of a patient positioning surface used in accordance with an embodiment of the present invention.
Figure 2B:
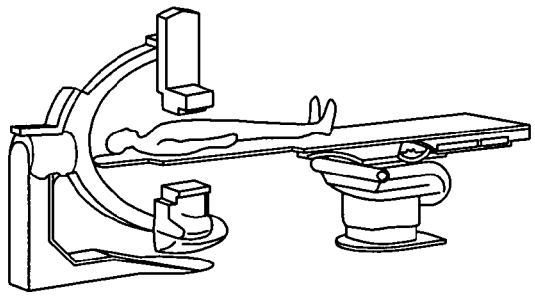
Figure 2C:
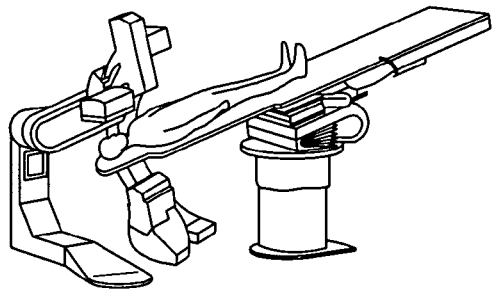
Figure 2D:
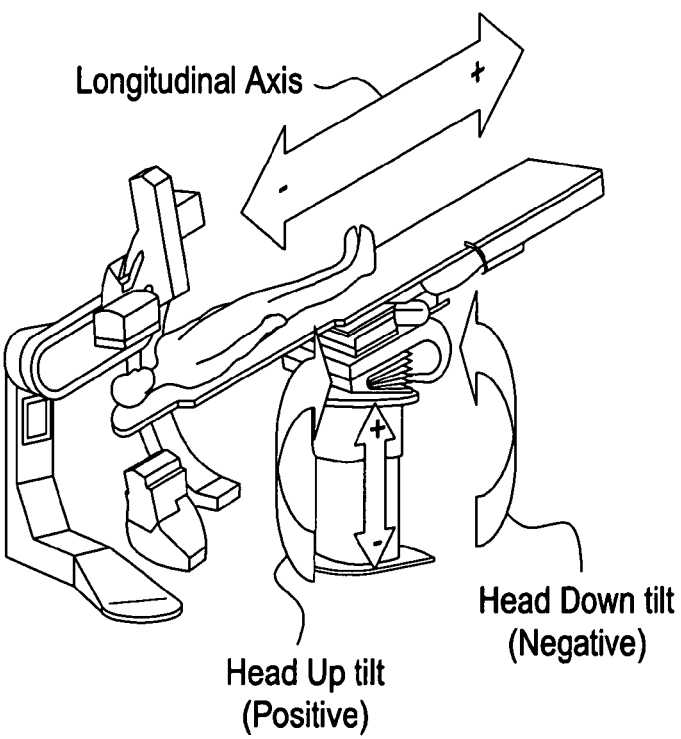
Figure 3A:
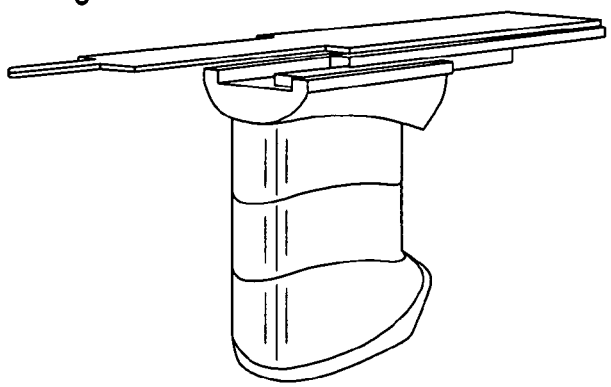
FIGS. 3A, 3B 3C and 3D illustrate positions of a patient positioning surface used in accordance with an embodiment of the present invention.
Figure 3B:
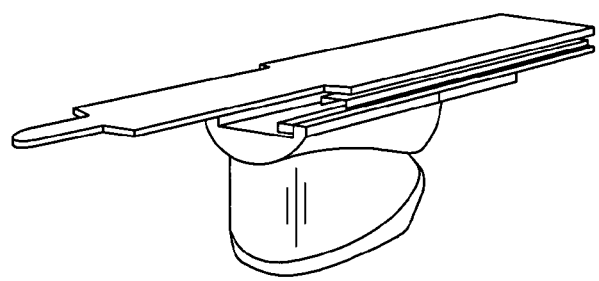
Figure 3C:
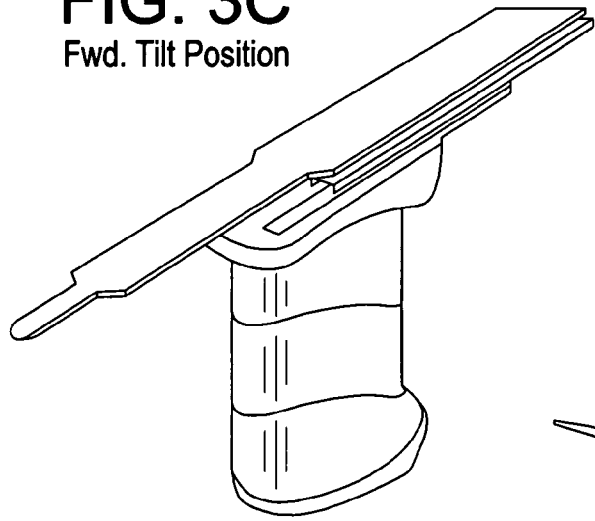
Figure 3D:
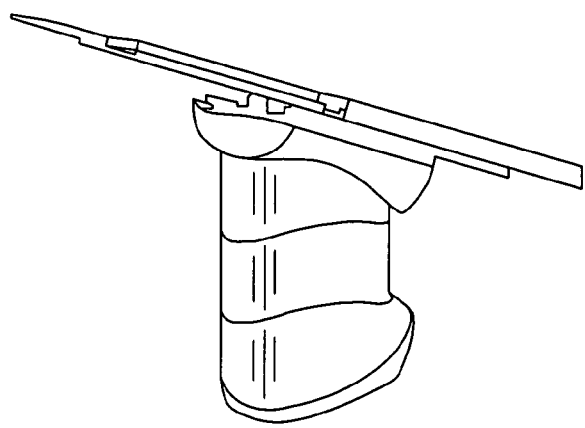

FIGS. 1A and 1B illustrate a patient positioning system 100 that is used in accordance with an embodiment of the present invention. The patient positioning system 100 includes a patient positioning surface 105, a base 110, a telescopic lift system 120, a longitudinal system 130, a tilt system 140, a lateral system 150 and a rotation system 160. The patient positioning system 100 is grouted, or fixed to the floor at the table base 110. The system 100 also includes a motion control system 170 (not pictured). The patient positioning system is described in more detail in U.S. Patent Application entitled "Grouted Tilting Patient Positioning Table for Vascular Applications," Application Ser. No. 10/065,866, filed on Nov. 26, 2002, with inventors Muthuvelan Varadharajulu, Rajagopal Narayanasamy, Baskar Somasundaram, and Shaji Alakkat. The application is herein incorporated by reference including the specification, drawings, claims, abstract, and the like. Additionally, the following U.S. Patent Applications are also incorporated by reference: "Method and Apparatus for Collision Avoidance in a Patient Positioning Platform,"Application Ser. No. 10/248,759, filed on Feb. 25, 2003, with inventor Muthuvelan Varadharajulu; "Synchronization Drive for a Longitudinal Axis Telescopic Guidance Mechanism,"filed on Mar. 4, 2003, with inventor Baskar Somasundaram; and "Method and Apparatus for Tilting in a Patient Positioning System, "filed on Mar. 4, 2003, with inventor Shaji Alakkat.

To enhance loading and unloading of a patient, the patient positioning surface 105 may rotate around a vertical axis using the rotation system 160. The patient positioning surface 105 may also be manually rotated about the rotation system 160. To move the patient to an image area, the patient positioning surface 105 may move vertically using the telescopic lift system 120 from a height at which the patient may be conveniently loaded to a height where imaging may occur (780 mm to 1080 mm, for example). To move a portion of the patient's body into the image area, the patient positioning surface 105 may move in a lateral direction (+/−140 mm from a normal imaging position, for example) using the lateral system 150. FIGS. 2 and 3 illustrate exemplary positions of the patient positioning surface 105 used in accordance with certain embodiments of the present invention.

Figure 4A:
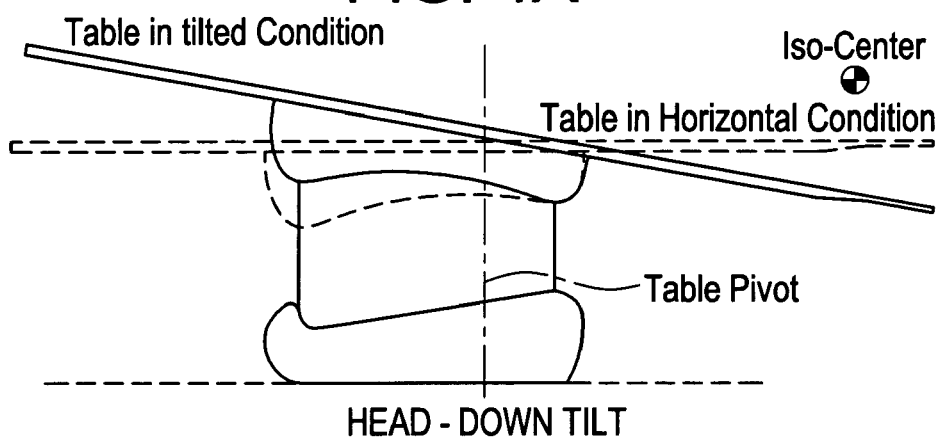
FIGS. 4A. 4B and 4C depict a tilting of a patient positioning surface with and without iso-center tracking used in accordance with an embodiment of the present invention.
Figure 4B:
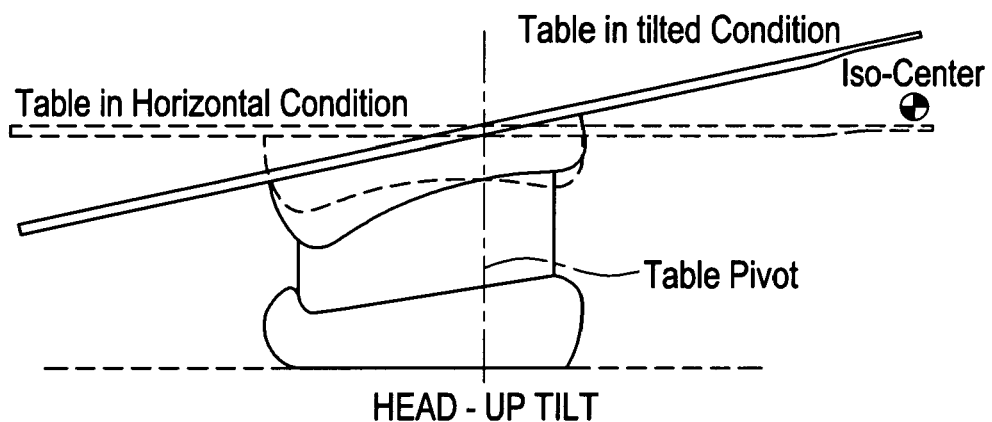
Figure 4C:
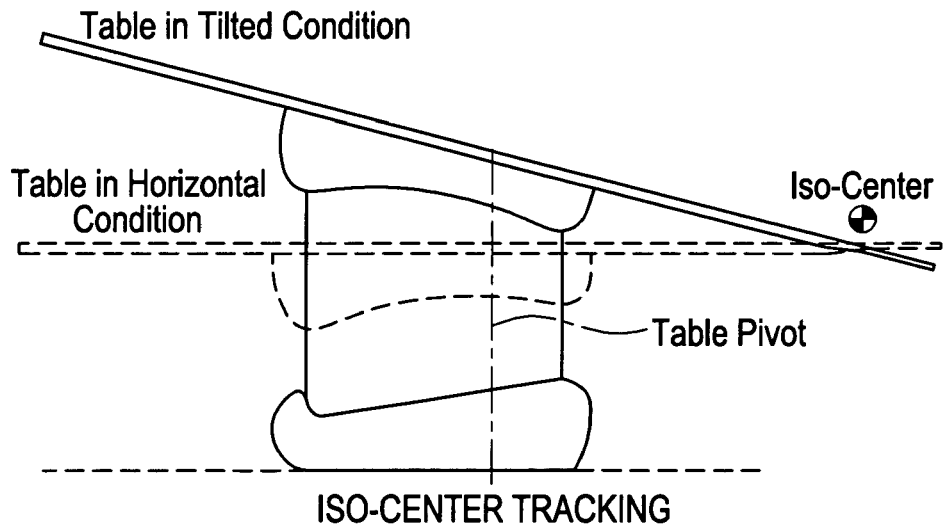

Additionally, the telescopic lift system 120 may provide a stroke or lift motion for iso-center tracking. Iso-center is the point at which three axes of an x-ray imaging system gantry meet (not shown). Iso-center tracking maintains a patient region of interest at the iso-center during tilt or other movement of the patient positioning system 100. Additional stroke for iso-center tracking is provided by the telescopic lift system 120 supported by a telescopic guide mechanism to accommodate a moment resulting from overhanging load. FIGS. 4A. 4B and 4C depict a tilting of the patient positioning surface 105 with and without iso-center tracking used in accordance with an embodiment of the present invention.

For head to toe coverage of the patient, the patient positioning system 100 may use longitudinal motion from the longitudinal system 130. For bolus chasing (following a bolus or contrast agent through a patient's blood vessels), the longitudinal motion may be motorized with a variable speed motor (2 to 15 cm/sec, for example) using the longitudinal system 130 and a guide mechanism. In a certain embodiment, in addition to motorized motion, lateral and longitudinal axes include a clutch to support manual panning of the patient positioning surface 105. That is, the clutch may be released to allow the patient positioning surface 105 to be positioned manually by an operator.

For emerging vascular procedures, such as emergent situations (falling artery pressure, for example), venous access and $CO_2$ studies, the patient positioning surface 105 may tilt head up and head down in the longitudinal direction (12 degrees up and 20 degrees down, for example). A region of interest of the patient may remain at the iso-center or the image area when the patient positioning surface 105 is tilted. In an embodiment, the region of interest remains in the iso-center or the image area using synchronized motion of the telescopic lift system 120, the longitudinal system 130 and the tilt system 140 as defined by the Inverse Kinematics Formula.

In an embodiment, mechanical and electrical interlocks and position feedback from the patient positioning system 100 help to ensure patient safety. Patient restraints may be provided to keep the patient on the patient positioning surface 105 and to help ensure patient safety. Certain embodiments of the patient positioning system 100 help to ensure a high level of patient safety through effective safety interlock systems and redundant systems for avoiding single point failures.

Safety interlocks and redundant safety systems are provided to help ensure patient safety in the patient positioning system 100. In an embodiment, all axes in the patient positioning system 100 are designed to have position encoders to read the coordinates of the patient positioning surface 105 at any position at any time. Ground clearance of the patient positioning surface 105 is calculated, and motion of the patient positioning surface 105 stops if the ground clearance is less than or equal to a specified safe limit. Thus, collisions may be avoided.

In a certain embodiment, all axes are designed with redundant safety systems to avoid single point failures and to help ensure patient safety. Each motorized axis of the patient positioning system 100 may include an incremental encoder and brake (on the drive or motor side). Each motorized axis may also include an absolute encoder and brake at the load side. During normal operation, the brake at the drive side operates to stop any axis of motion. If a problem arises in the driveline, a difference in incremental encoder (drive side) and absolute encoder (load side) readings operates the brake at the load side to stop the axis. Additionally, both power-on and power-off brakes may be activated during procedures to ensure stability and rigidity of the patient positioning surface 105. During power-off conditions, only the power-off brake may be activated to allow easy removal of the patient by rotating the patient positioning surface 105.

The patient positioning surface 105 may be prevented from tilting at the lowest position of the patient positioning surface 105, since the lowest position of the patient positioning surface 105 is used for easy loading and unloading of the patient. Each axis is provided with a power-off brake to lock the motion during a power failure and/or any malfunction of the motors and servo drives. Each axis is provided with a software limit, a hardware limit, and mechanical hard stops. An example of a software limit is the following: during normal operations, the patient positioning surface 105 shall not move beyond a certain point. An example of a hard limit is the following: the patient positioning surface 105 is controlled by a limit switch. The limit switch stops the motion of the patient positioning surface 105 if a software malfunction occurs. An example of a mechanical hard stop is as follows: an end stop is provided as backup if both software and hardware limits fail. The coordinates of all axes may be continuously monitored to avoid a collision with the ground and/or predetermined objects.

The following are some examples of operations involving the patient positioning system 100. The examples are provided to illustrate use of components and systems in a patient positioning system 100 and are not intended to be a comprehensive list.

For example, a patient may be loaded on the patient positioning surface 105. First, the patient positioning surface 105 is positioned at 780 mm from the ground using the telescopic lift system 120. Then, the patient positioning surface 105 is rotated to the right-hand or left-hand side using the rotation system 160. Next, the patient is loaded onto the patient positioning surface 105. Patient restraints may be used to secure the patient on the patient positioning surface 105. To unload the patient, the patient positioning surface 105 is rotated to the right-hand or left-hand side using the rotation system 160. The patient positioning surface 105 is repositioned to a height of 780 mm from ground level by the lift system 120. The patient restraints are unlocked, and the patient is removed from the patient positioning surface 105.

Also, for example, the patient may be moved into the image area. First, the rotation system 160 rotates the patient positioning surface 105 to zero degree. Next, the patient positioning surface 105 is moved vertically to the image area using the telescopic lift system 120. Then, the patient positioning surface 105 is adjusted laterally in the image area with the lateral system 150. The patient positioning surface 105 may also be adjusted longitudinally by the longitudinal system 130 to reach a desired position in the image area.

A patient may be positioned on the patient positioning surface 105 for several medical procedures and examinations. For example, in angiography, a patient's height may be adjusted by raising and lowering the patient positioning surface 105 using the telescopic lift system 120. Additionally, four-way panning may be accomplished using the lateral system 150 and the longitudinal system 130. For peripheral angiography, the patient positioning surface 105 may also be rotated into proper position using the rotation system 160 and tilted using the tilt system 140.

For bolus chasing, patient restraints may be used to secure the patient on the patient positioning surface 105. The longitudinal system 130 advances the patient positioning surface 105 in the longitudinal direction in bolus mode (0–15 cm/sec). For venous access and $CO_2$ studies, for example, patient restraints may keep the patient in touch with the patient positioning surface 105, and the lift 120, longitudinal 130, and tilt 140 systems may be used for iso-center tracking to maintain a desired image area during movement. In emergent situations, restraints secure the patient on the patient positioning surface 105, and the tilt system 140 tilts the patient to a desired position.

Cardiac pulmonary resuscitation (CPR) is a procedure performed for patients who suffer from cardiac arrest, for example. In order to bring a patient to a CPR position if the patient positioning surface 105 is in a horizontal position, the patient positioning surface 105 is moved longitudinally in a backward direction using the longitudinal system 130. Then, the patient positioning surface 105 is lowered using the lift system 120. If the patient positioning surface 105 is titled, the tilt system 140 returns the patient positioning surface 105 to a horizontal position. Then, the longitudinal system 130 moves the patient positioning surface 105 backward, and the lift system 120 lowers the patient positioning surface 105 to enable CPR to be performed on the patient.

The telescopic lift system 120 is used by the patient positioning system 100 to accommodate high load, moments, and lift motion or stroke to position a patient in the image area. The tilt system 140 allows the patient positioning system 100 to tilt head up or head down and maintain a desired image through iso-center tracking. The patient positioning system 100 includes a lateral system 150 to move the patient positioning surface 105 laterally using motorized and/or manual panning.

The patient positioning system 100 supports motorized bolus chasing with head to toe coverage so that an image may be traced as the contrast agent travels through the patient. The patient positioning system 100 tracks the coordinates of the patient positioning surface 105. Positioning tracking facilitates collision avoidance with the ground and/or other predetermined objects. Tracking also allows the patient positioning system 100 to return the patient positioning surface 105 to a previously recorded and/or memorized position.

Examples of complex motion of the patient positioning system 100 have been described above. Execution of complex motions to position the patient positioning surface 105 for various medical procedures creates a risk of collision between the patient positioning surface 105 and the ground and/or another object in the examination room. Certain embodiments of the present invention provide a system and method for collision avoidance.

The motion control system 170 for the patient positioning system 100 includes three major parts: a user interface, an I/O board, and servo nodes (not shown). A user may move the patient positioning surface 105 using the user interface. User interface commands are processed by the I/O board (CPU). Commands are then sent to corresponding servo nodes that control the respective axis movements. In an embodiment, a Power PC-based micro controller is used as the CPU. An application program, which is running on a real-time operating system, may control the patient positioning system 100.

Clearance between the patient positioning surface 105 and the ground and/or another object is determined dynamically based on the positions of the lift, longitudinal, and tilt axes in the patient positioning system 100. The motion control system 170 may store a safe clearance value. The motion control system 170 determines the clearance between the patient positioning surface 105 and the ground or another object. The motion control system 170 compares the measured clearance and the safe clearance value. The motion control system 170 stops movement of axes of the patient positioning system 100 if the measured clearance is less than or equal to the stored safe clearance.

Figure 5:
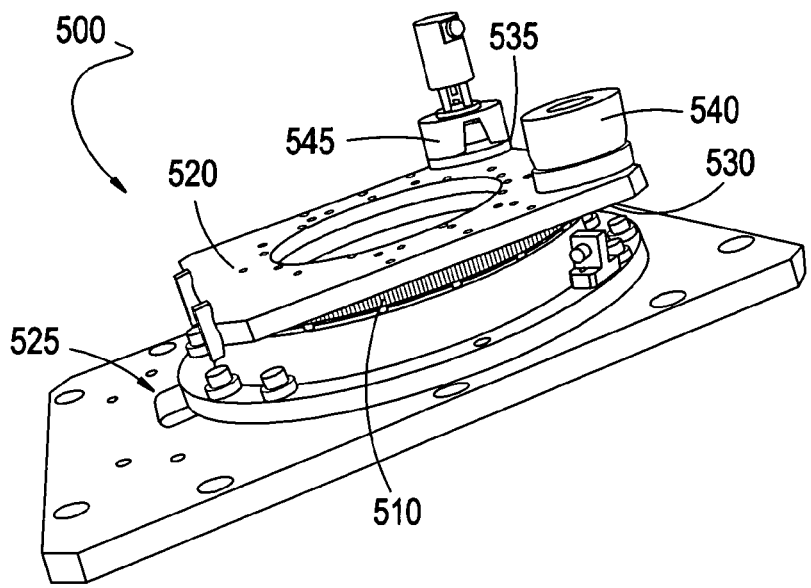
FIG. 5 shows a rotational axis braking system in a patient positioning system used in accordance with an embodiment of the present invention.
Figure 6A:
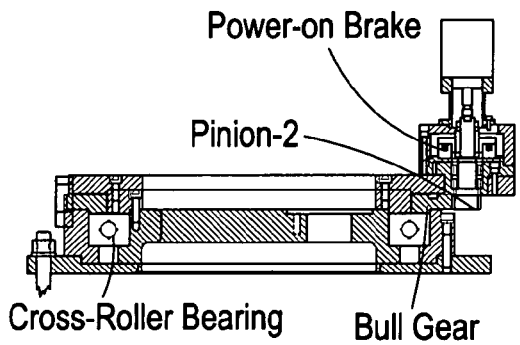
FIGS. 6A and 6B show a rotational axis braking system in a patient positioning system used in accordance with an embodiment of the present invention.
Figure 6B:
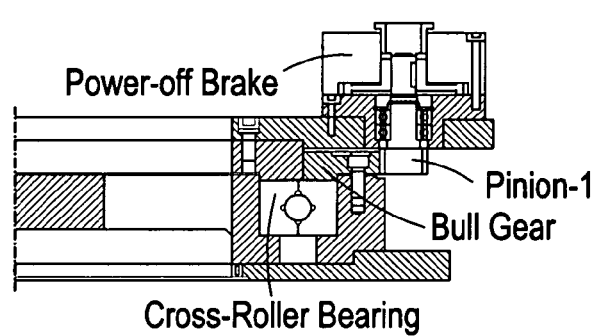

FIG. 5 shows a rotational axis braking system 500 in a patient positioning system 100 used in accordance with an embodiment of the present invention. FIGS. 6A and 6B show a cross-sectional view of a rotational axis braking system 500 in a patient positioning system 100 used in accordance with an embodiment of the present invention. The rotational axis braking system 500 works, for example, with the rotation system 160 described above in relation to FIGS. 1A and 1B and the patient positioning system 100. The rotational axis and brake system 500 includes a bull gear 510, a bearing clamping plate 520, a bearing housing 525, pinions 530, 535, a power-off brake 540, and a power-on brake 545. In an embodiment, the patient positioning surface 105 rotates manually. The rotation and brake system 500 rotates the patient positioning surface 105 about the vertical axis (+/−90 degrees, for example). The rotational axis braking system 500 may include a docking mechanism for locating a zero position (0 degrees in the rotation axis) easily.

In an embodiment, the bull gear 510 is stationary. Two pinions 530, 535 are mounted at 90 degrees, for example, on the bearing housing 525. The pinions 530, 535 mesh with the bull gear 510 and rotate along with the main structure of the patient positioning system 100. A power-off brake 540 is mounted directly onto the pinion 530. A power-on brake 545 is mounted onto the pinion 535. When the brake 540, 545 is applied, the pinion 530, 535 holds the main structure against the stationary bull gear 510.

In an embodiment, the brake and pinion arrangement is a positive arrangement. Using gear drive allows for torque multiplication. Size of the brake 540, 545 is reduced using a higher gear ratio between the bull gear 510 and the braking pinions 530, 535. A small breaking torque at the pinion 530, 535 is multiplied by the gear ratio to maximize a holding torque.

The power-on brake 545 is active when power is supplied to the brake 545. The power-off brake 540 is active when power is shut off or removed from the brake 540. Both power-on and power-off brakes 540, 545 may be activated to help ensure stability and rigidity of the patient positioning surface 105. When power is off, only the power-off brake 540 may be activated for ease in removing the patient from the patient positioning surface 105, for example.

In an embodiment, the combination of power-on and power-off brakes 540, 545 results in three states. In the first state, power is supplied to the power-on brake 545, and no power is supplied to the power-off brake 540 (100% capacity). Both brakes 540, 545 hold the patient positioning surface 105 through pinions 530, 535 and provide a rigid connection. During procedures (i.e., during imaging and while loading the patient onto the patient positioning surface 105), power is supplied to the power-on brake 545, and both brakes 540, 545 hold the patient positioning surface 105.

In the second state, no power is supplied to both the power-on brake 545 and the power-off brake 540 (50% capacity). In a power fail condition, the power-off (failsafe) brake 540 engages (catches), but the power-on brake 545 is released. Thus, the patient positioning surface 105 may be rotated with less effort to unload a patient, for example. In an alternative embodiment, power may be supplied to the power-on brake 545 and to the power-off brake 540, also resulting in a 50% capacity state.

In the third state, power is supplied to the power-off brake 540 and not to the power-on brake 545 (0% capacity). Thus, both brakes 540, 545 are released, and the patient positioning surface 105 may be used for repeating imaging scans at an angle, for example. The freely moving patient positioning surface 105 may also be used after loading the patient to bring the patient positioning surface 105 to the zero position.

FIG. 7 illustrates a flow diagram for braking in a patient positioning system in accordance with an embodiment of the present invention. First, at step 710, power is supplied to the power-on brake 545, and no power is supplied to the power-off brake 540 to lock the patient positioning surface 105. Then, at step 720, the patient is loaded onto the patient positioning surface 105.

Next, at step 730, power is supplied to the power-off brake 540, and no power is supplied to the power-on brake 540. Thus, both brakes 540, 545 are released, and the patient positioning surface 105 is free to rotate. Then, at step 740, the patient positioning surface 105 is rotated to a desired imaging position.

At step 750, power is supplied to the power-on brake 545 but not the power-off brake 540. This locks the patient positioning surface 105 and keeps the patient positioning surface 105 rigid. Then, at step 760, image scans of the patient are obtained.

Next, at step 770, power is removed from the power-on brake 545 and supplied to the power-off brake 540. At step 780, the patient positioning surface 105 is returned to the zero position. Then, at 790, no power is supplied to either the power-on brake 545 or the power-off brake 540 (e.g., a power failure). At 795, the patient positioning surface 105 may be rotated with less effort to unload the patient.

Thus, certain embodiments of the present invention allow minimal or no disturbance of the patient positioning surface 105 during imaging since both power-on and power-off brakes 540, 545 secure the patient positioning surface 105 rigidly. Increased safety is provided during patient loading and unloading since both power-on and power-off brakes 540, 545 secure the patient positioning surface 105 rigidly. Certain embodiments allow free rotation of the patient positioning surface 105 to any angle by releasing both brakes 540, 545. A positive braking system using a gear and pinion drive minimizes the possibility of patient positioning surface 105 slippage. That is, gear teeth are used instead of friction. The teeth on the bull gear 510 lock with teeth on the pinion 530, 535 to brake. The size of the brakes 540, 545 is reduced since the gear ratio provides enough torque. Thus, the cost of the unit and the overall size of the unit are reduced.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A patient positioning system for medical applications, said system comprising:
   a patient positioning surface for supporting a patient;
   a lift subsystem for adjusting elevation of said patient positioning surface;
   a longitudinal subsystem for moving said patient positioning surface in a longitudinal direction;
   a tilt subsystem for tilting said patient positioning surface;
   a rotation subsystem for rotating said patient positioning surface;
   a first brake and a second brake for securing said patient positioning surface,
   wherein said first brake and said second brake hold said patient positioning surface through torque multiplication;
   a position sensor for determining a position of said patient positioning surface; and
   a control subsystem for controlling operation of said patient positioning system.

2. The system of claim 1, wherein said first brake comprises a power-off brake, said power-off brake active when power is removed from said power-off brake.

3. The system of claim 1, wherein said second brake comprises a power-on brake, said power-on brake active when power is applied to said power-on brake.

4. The system of claim 1, wherein a bull gear and pinion are used in combination with said first brake and said second brake to secure said patient positioning surface.

5. The system of claim 1, wherein said first brake and said second brake secure said patient positioning surface using interlocking teeth.

6. The system of claim 1, wherein said first brake and said second brake are used in combination to secure said patient positioning surface.

7. The system of claim 1, wherein said first brake and said second brake may be used in at least three states, said at least three states including:
   a 100% capacity state with said first and second brakes activated;
   a 50% capacity stale with said first brake released and said second brake activated; and
   a 0% capacity, state with said first and second brakes released.

8. The system of claim 1, wherein said first brake is mounted on a first pinion and said second brake is mounted on a second pinion.

* * * * *

UNITED STATES PATENT AND TRADEMARK OFFICE
CERTIFICATE OF CORRECTION

PATENT NO. : 7,028,356 B2
APPLICATION NO. : 10/379122
DATED : April 18, 2006
INVENTOR(S) : Baskar Somasundaram It is certified that error appears in the above-identified patent and that said Letters Patent is hereby corrected as shown below:

At col. 10, line 20, claim 7, delete "stale" and insert --state--.

At col. 10, line 22, claim 7, delete "," after "capacity".

Signed and Sealed this

Eighth Day of August, 2006

JON W. DUDAS
*Director of the United States Patent and Trademark Office*